(12) United States Patent
Huang et al.

(10) Patent No.: US 7,399,881 B1
(45) Date of Patent: Jul. 15, 2008

(54) TRANSESTERIFICATION PROCESS OF METHYL ACETATE

(75) Inventors: Hsiao-Ping Huang, Taipei (TW); Cheng-Ching Yu, Taipei (TW); Ming-Jer Lee, Taipei (TW); Jyun-Hong Chen, Taipei (TW); Jian-Kai Cheng, Changhua County (TW)

(73) Assignee: National Taiwan University, Taipei (TW)

( * ) Notice: Subject to any disclaimer, the term of this patent is extended or adjusted under 35 U.S.C. 154(b) by 34 days.

(21) Appl. No.: 11/715,776

(22) Filed: Mar. 8, 2007

(30) Foreign Application Priority Data

Dec. 29, 2006 (TW) .............................. 95150090 A

(51) Int. Cl.
*C07C 67/02* (2006.01)

(52) U.S. Cl. ..................................................... 560/234
(58) Field of Classification Search ........................ None
See application file for complete search history.

(56) References Cited

U.S. PATENT DOCUMENTS 4,927,954 A * 5/1990 Knopf et al. ................. 558/441

OTHER PUBLICATIONS

Luyben, William L. et al., "Design and Control of Conventional and Reactive Distillation Processes for the Production of Butyl Acetate," *Ind. Eng. Chem. Res.* 2004, 43, 8014-8025.
Steinigeweg, Sven and Jurgen Gmehling, "Transesterification Processes by Combination of Reactive Distillation and Pervaporation," *Chemical Engineering and Processing*, 43 (2004) 447-456.

* cited by examiner

*Primary Examiner*—Karl Puttlitz
(74) *Attorney, Agent, or Firm*—Volpe and Koenig, P.C.

(57) ABSTRACT

A transesterification process of methyl acetate is provided. The process comprises: (a) performing a first reactive distillation of a methyl acetate solution and a first alcohol to generate a first ester and a first mixture; (b) performing a first distillation of a first part of the first mixture to generate a second mixture; and (c) performing a second reactive distillation of a first part of the second mixture and a second alcohol to generate a second ester; wherein the respective one of the first and second alcohols is a limiting reagent. The transesterification process provided in the present invention could highly reduce the investing production cost of the transesterification of the by-product, methyl acetate, in the conventional polyvinyl alcohol plants.

17 Claims, 1 Drawing Sheet

TRANSESTERIFICATION PROCESS OF METHYL ACETATE

FIELD OF THE INVENTION

The present invention relates to a transesterification process, and more particularly to a transesterification process of methyl acetate.

BACKGROUND OF THE INVENTION

Polyvinyl alcohol is a kind of polymer widely used in the chemical industry; however, the manufacturing process of polyvinyl alcohol is always accompanying with the abundant production of the by-product, methyl acetate. Methyl acetate is a less valuable solvent due to its low industrial application and low volatility, even if the amount of the produced methyl acetate is one-half times higher than that of polyvinyl alcohol. Accordingly, the impure methyl acetate is usually discharged into the atmosphere after scrubbing in a wastewater treatment system or burned in an incinerator. In view of the above, if methyl acetate could be recycled to be efficiently transesterified into other kinds of esters having higher economical value, the working performance of the polyvinyl alcohol plants will be highly increased. In recent years, the transesterification processes of methyl acetate have been developed as below.

(1) Luyben et al (2004) proposed one transesterification process of methyl acetate. The transesterification process was performed by combination of a reactive distillation tower, a conventional distillation tower and a distillation tower of high pressure. Firstly, the conventional distillation tower has two feeding stream of methyl acetate; one is the mixture of methyl acetate and methanol, and the other is the reflux stream of the abundant methanol and methyl acetate from the top of the reactive distillation tower. The conventional distillation tower functions as separating methyl acetate from methanol. Methanol could be thus obtained from the bottom of the conventional distillation tower, whereas the azeotrope of methyl acetate and methanol could be formed on the top thereof.

The reactive distillation tower has also two feeding stream; one is the azeotrope, and the other is the reflux stream from the top of the distillation tower of high pressure, where the major composition of the stream is n-butanol. While the reflux of n-butanol is fed into the reactive distillation tower, another substream of fresh n-butanol is mixed simultaneously therewith to transfer into the upper portion of the reactive section in the reactive distillation tower, so that methyl acetate and n-butanol will react therein. Subsequently, one mixture of the abundant methanol and methyl acetate would be formed on the top of the reactive distillation tower, and then the mixture would be further refluxed into the conventional distillation tower to separate methyl acetate from methanol. Simultaneously, another mixture of n-butanol and butyl acetate would be obtained from the bottom of the reactive distillation tower, and the mixture is further introduced into the distillation tower of high pressure to separate n-butyl ester from butyl acetate.

The distillation tower of high pressure could break through the co-boiling point of n-butyl ester and butyl acetate by means of applying high pressure. Accordingly, the n-butanol could be formed on the bottom of the distillation tower of high pressure, whereas the substantial n-butanol is obtained from the top thereof, followed by refluxing the substantial n-butanol to the reactive distillation tower. Though the transesterification process of methyl acetate proposed by Luyben et al overcomes the co-boiling phenomenon of n-butyl ester and butyl acetate by means of the distillation tower of high pressure, the consumption of the steam amount of the distillation tower of high pressure brings about the considerable investing production cost to the conventional polyvinyl alcohol plants.

(2) Steinigeweg et al (2004) also proposed another transesterification process of methyl acetate. The process was performed by combination of a reactive distillation tower, a conventional distillation tower and a pervaporation device. The reactive distillation tower has two feeding streams; one is methyl acetate introduced from the lower portion of the reactive section thereof, and the other is n-butanol introduced from the upper portion of the reactive section thereof. Accordingly, the transesterified product, butyl acetate, would be obtained from the bottom of the reactive distillation tower and the mixture of methyl acetate and methanol would be formed on the top thereof.

Subsequently, the mixture is further introduced to the pervaporation device. By means of the pervaporation device, methyl acetate and methanol could be separated and respectively obtained with high purity. The separated methyl acetate with high purity as well as another fresh feeding stream of methyl acetate would be mixed and then introduced into the lower portion of the reactive section of the reactive distillation tower. Simultaneously, the separated methanol with high purity is introduced into the conventional distillation tower for a further separation, wherein the conventional distillation tower, methanol will be deposited on the bottom thereof, whereas the azeotrope of methyl acetate and methanol is formed on the top thereof. Then, the azeotrope is refluxed to the pervaporation device for a further separation of methyl acetate and methanol.

Though the transesterification process proposed by Steinigeweg et al overcomes the co-boiling phenomenon of methyl acetate and methanol by means of the pervaporation device, the regular placement of the film in the pervaporation device also lowers down the overall economic efficiency of the conventional polyvinyl alcohol plants.

In view of the mentioned drawbacks, a special transesterification process of methyl acetate with the competitive investing production costs and the higher conversion rate of methyl acetate is necessary for most polyvinyl alcohol plants.

From the above description, it is known that how to develop an efficient and economical transesterification process of methyl acetate has become a major problem to be solved. In order to overcome the drawbacks in the prior art, an improved transesterification process of methyl acetate is provided. The particular design in the present invention not only solves the problems described above, but also is easy to be implemented. Thus, the invention has the utility for the industry.

SUMMARY OF THE INVENTION

In consideration of a transesterification process of methyl acetate working in the polyvinyl alcohol plants with a more economic and efficient operation, a cost-saving transesterification of methyl acetate is needed.

In accordance with one aspect of the present invention, a transesterification process of methyl acetate is provided, which comprises the following steps: (a) performing a first reactive distillation of a methyl acetate solution and a first alcohol to generate a first ester and a first mixture; (b) performing a first distillation of a first part of the first mixture to generate a second mixture; and (c) performing a second reactive distillation of a first part of the second mixture and a second alcohol to generate a second ester, wherein the respective one of the first and second alcohols is a limiting reagent.

Preferably, the methyl acetate solution includes a 40 mol % methanol.

Preferably, the respective reactive distillation is operated in a temperature ranged from 55° C. to 170° C. and the step (b) is operated in a temperature ranged from 55° C. to 65° C.

Preferably, the respective reactive distillation and the distillation are operated in a pressure ranged from 1 to 2 atmosphere pressure.

Preferably, the step (b) further comprises a step of performing a third reactive distillation of a second part of the first mixture and a third alcohol to generate a third ester.

Preferably, the first, second and third alcohols are ones selected from a group consisting of an ethanol, an isopropanol, a propanol, an isobutanol, a butanol, an isoamyl alcohol, an amyl alcohol, and a hexyl alcohol, and the first, second and third esters are the same ester.

Preferably, the step (b) further comprises generating a first methanol therefrom and a step of performing a second distillation of a second part of the second mixture to generate a second methanol. In accordance with another aspect of the present invention, a further transesterification process of methyl acetate is provided, which comprises the following steps: (a) reacting a methyl acetate solution with a first alcohol in a reactive distillation device to generate a first mixture and a first ester; (b) performing a first distillation of a first part of the first mixture in a distillation device to generate a second mixture; and (c) reacting a first part of the second mixture and a second alcohol in the reactive distillation device to generate a second ester, wherein the respective one of the first and the second alcohols is a limiting reagent.

Preferably, the reactive distillation device comprises a plurality of reactive trays, a plurality of stripping trays and a plurality of rectifying trays, and a number of the plurality of reactive trays is ranged from 15 to 55, a number of the plurality of stripping trays is ranged from 3 to 10, and a number of the plurality of rectifying trays is ranged from 5 to 20.

Preferably, the alcohols are fed from an upper portion of the reactive distillation device and the methyl acetate solution is fed from a portion being positioned from a middle portion to a lower portion of the reactive distillation device.

In accordance with a further aspect of the present invention, another transesterification process of methyl acetate is provided, which comprises the following steps: (a) performing a first distillation of a methyl acetate solution to generate a first methanol and a first mixture; (b) performing a first reactive distillation of a first part of the first mixture and a first alcohol to generate a first ester and a second mixture; and (c) performing a second distillation of a first part of the second mixture to generate a second methanol, wherein the first alcohol is a limiting reagent.

Preferably, the step (b) further comprises a step of performing a third distillation of a second part of the first mixture to generate a third methanol.

Preferably, the process further comprises a step of (d) performing a second reactive distillation of a second part of the second mixture and a second alcohol to generate a second ester.

Preferably, the first and second alcohols are ones selected from a group consisting of an ethanol, an isopropanol, a propanol, an isobutanol, a butanol, an isoamyl alcohol, an amyl alcohol, and a hexyl alcohol, and the first and the second esters are the same ester.

Preferably, the first and the second reactive distillations are performed in a reactive distillation device.

Preferably, the alcohols are fed from an upper portion of the reactive distillation device and the methyl acetate solution is fed from an upper portion of the distillation device.

The above aspects and advantages of the present invention will become more readily apparent to those ordinarily skilled in the art after reviewing the following detailed descriptions and accompanying drawings, in which:

DETAILED DESCRIPTION OF THE PREFERRED EMBODIMENT

Figure 1:
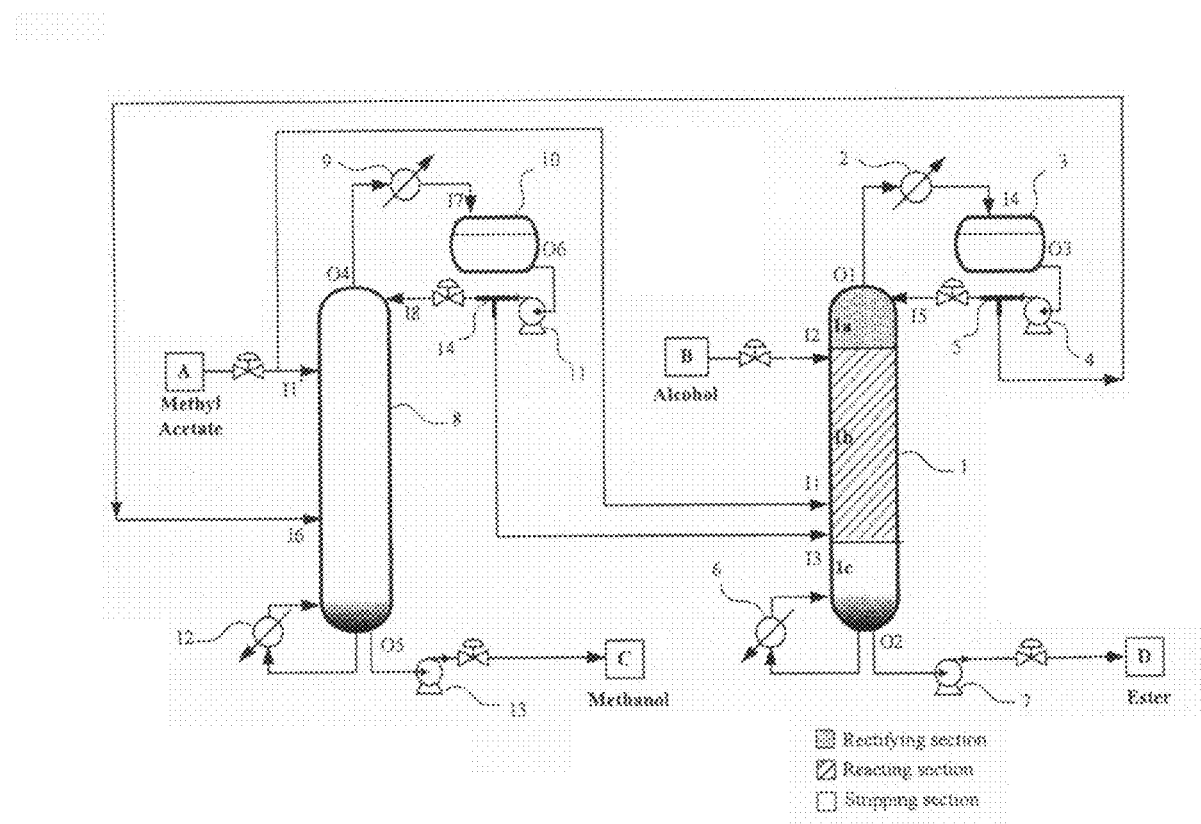
FIG. 1 is a schematic diagram of the transesterification process of methyl acetate according to a preferred embodiment of the present invention.

The present invention will now be described more specifically with reference to the following embodiments. It is to be noted that the following descriptions of preferred embodiments of the present invention are presented herein for the purposes of illustration and description only; it is not intended to be exhaustive or to be limited to the precise form disclosed.

A reaction formula of the transesterification reaction of methyl acetate is shown below:

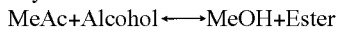

MeAc+Alcohol ⟷ MeOH+Ester

The mentioned abbreviation "MeAc" represents methyl acetate and the abbreviation "MeOH" represents methanol.

The transesterification reaction of methyl acetate is a reversible reaction and possesses the low equilibrium constant. The feeding of methyl acetate is regarded as a controlling limited factor in the transesterification reaction of methyl acetate of the present invention, and thus the reaction will be towards the generation of the transesterified product. Accordingly, it is preferred to feed the excess amount of methyl acetate to promote the reaction towards the generation of the transesterified product.

In consideration of the physical properties of the transesterification system of methyl acetate into butyl acetate in its entirety, the priority of the boiling points of each constituent existing therein is shown in Table (1).

TABLE (1)

| Constituents | Boiling Point (° C.) |
| --- | --- |
| Methyl acetate/Methanol | 53.57 |
| Methyl acetate | 57.05 |
| Methanol | 64.53 |
| n-Butanol/Butyl acetate | 116.9 |
| n-Butanol | 117.7 |
| Butyl acetate | 126.0 |

In the transesterification system of methyl acetate into butyl acetate, methyl acetate will react with n-butanol to generate methanol and butyl acetate. In such transesterification system, the possible azeotropes include two binary-components, methyl acetate and methanol together with butyl acetate and n-butanol. Furthermore, methyl acetate is the lightest component and easily tends to form the azeotrope with methanol.

The catalysts required for the transesterification reaction could be one of the heterogeneous catalysts and homogeneous catalysts. In the transesterification process of methyl acetate of the present invention, heterogeneous solid catalysts are utilized to promote the reaction. The solid catalysts superiors in the convenience that they be packed anywhere within the reactor (e.g. the bottom and the top thereof, the reflux device, etc.), so that the reaction section could be selected flexibly to be disposed within the reactor, and the problem to recycle the liquid catalyst could be solved accordingly.

Ion exchange resins are generally chosen as the solid catalysts, such as Amberlyst® 15 (Rohm and Hass) or Purolite CT179 (Purolite) commonly used in industry. In addition, Katapak-S is commonly adopted as the packing structure of the solid catalysts or the packings of the solid catalysts are disposed within the trays via a fixed device (Davy Process Technology).

Please refer to FIG. 1, which depicts a schematic diagram of the transesterification process of methyl acetate according to a preferred embodiment of the present invention. The major components for performing the transesterification process of methyl acetate are a reactive distillation system, a reflux system, and a distillation system.

The reactive distillation system comprises a reactive distillation device (1), input pipes (I1-I3, and I5), an output pipe (O1) and another output pipe (O2). The reactive distillation device (1) is disposed with a rectifying section (1a), a reactive section (1b) and a stripping section (1c), wherein the rectifying section (1a) is further disposed with a plurality of rectifying trays, the reactive section (1b) is disposed with a plurality of reactive trays, and the stripping area (1c) is disposed with a plurality of stripping trays. The plurality of reactive trays (1b) are packed with ion exchange resins (Amberlist® 15) for increasing the reaction efficiency.

An alcohol solution (the n-butanol solution is exemplified in the following detailed description) from an alcohol solution tank (B) is fed into an upper portion of the reactive section (1b) of the reactive distillation device (1) via the input pipe (I2). A methyl acetate solution is fed into a lower portion of the reactive section (1b) via the input pipe (I3). Therefore, the n-butanol solution and the methyl acetate solution will proceed a transesterification reaction in the reactive section (1b), where the transesterified product, butyl acetate, will be deposited on the bottom of the reactive distillation device due to its highest boiling point in the transesterification system.

Furthermore, a re-boiling device (6) is disposed beneath the bottom of the reactive distillation device (1) to heat the butyl acetate liquid deposited on the bottom of the reactive distillation device (1), which promotes a further separation of other residues existing in the butyl acetate liquid.

The reactive distillation device (1) allows the methyl acetate solution and the n-butanol solution to perform the transesterification reaction, and thus the existing components in the reactive distillation device (1) theoretically include methyl acetate, n-butanol, methanol and butyl acetate after the transesterification. However, n-butanol is controlled as the limiting reagent so it could easily consumed completely and immediately. Since the boiling point of butyl acetate is highest, the continuous heating process operated by the re-boiling device (6) make methyl acetate and methanol of the lower boiling point convert from a liquid phase to a gaseous one whereby the gaseous methyl acetate and methanol will rise to the top of the reactive distillation device (1). Consequently, the ester product, butyl acetate, will be deposited on the bottom of the reactive distillation device (1) and obtained in high purity. Then, butyl acetate is discharged from the output pipe (O2) through a pump (7) to an ester reservoir (D). The mixture formed by methanol and the unreacted methyl acetate on the top of the reactive distillation device (1) is named as a first mixture herein.

The reactive distillation system in the present invention further comprises a first condensing system. The first condensing system comprises a condenser (2) and the relevant connecting tubes, where the condenser (2) is coupled to the reactive distillation device (1), so as to liquefy the first mixture from the reactive distillation device (1).

The reflux system in the transesterification process of methyl acetate of the present invention comprises a reflux device (3), a pump (4), a T-type bypassing tube (5), an input pipe (I4), and an output pipe (O3). The first mixture is discharged from the output pipe (O1) of the reactive distillation device (1), followed by being liquefied in the condenser (2), and then fed to the reflux device (3) via the input pipe (I4). The reflux device (3) is respectively coupled to the condenser (2) and the T-type bypassing tube (5). The liquefied first mixture proceeds a refluxation in the reflux device (3), and then is discharged via the output pipe (O3) by the pump (4) to the T-type bypassing device (5). The T-type bypassing device (5) bypasses a first portion of the refluxed first mixture into the distillation device (8), which the major composition of the first portion is methanol, and bypasses a second portion of the refluxed first mixture into the reactive distillation device (1), which the major composition of the first portion is methyl acetate, for continuously proceeding a further transesterification.

The distillation system in the transesterification process of methyl acetate comprises a distillation device (8), the input pipe (I'1), an input pipe (I6), another input pipe (I8), an output (O4) and another output pipe (O5). The first portion of the first mixture is introduced to the distillation device (8) via the input pipe (I6) for a further distillation.

Moreover, a re-boiling device (12) is disposed beneath the bottom of the distillation device (8) to heat the liquid deposited thereon. As the boiling point of methanol is higher than that of methyl acetate, the continuous heating process operated by the re-boiling device (12) makes the methyl acetate in the first portion of the first mixture convert from a liquid phase to a gaseous one, and thus the gaseous methyl acetate rise to the top of the distillation device (8). Such process makes the methanol solution deposited on the bottom of the distillation device (8) achieve a higher purity continuously. Then, the methanol solution of higher purity is discharged via the output pipe (O5) by the pump (13) and followed by sending to a methanol reservoir (C). The compositions of the gaseous mixture risen to the top of the distillation device (8) are respectively butyl acetate and n-butanol in a rare amount together with methanol and water in a higher amount, where the gaseous mixture is named as a second mixture herein.

The methyl acetate solution is fed to the reactive distillation device (1) via the input pipe (I1) from a methyl acetate solution tank (A) or alternatively fed to the distillation device (8) via the input pipe (I1').

The transesterification process of methyl acetate in the present invention further comprises a second condensing system. The second condensing system comprises a condenser (9) and the relevant connecting tubes, where the condenser (9) is coupled to the distillation device (8), so as to liquefy the second mixture from the distillation device (8).

Furthermore, the transesterification process of methyl acetate in the present invention further comprises another reflux system. The reflux system comprises a reflux device (10), a T-type bypassing device (14), a pump (11), an input pipe (I7) and an output pipe (O6). The reflux device (10) is coupled both to the condenser (9) and the T-type bypassing device (14). Subsequently, the second mixture on the distillation device (8) is sent to the reflux device (10), so that the second mixture is liquefied in the condenser (9), followed by sending to the reflux device (10) via the input pipe (I7). After the refluxation, the liquefied second mixture in the reflux device (10) is discharged via the output pipe (O6) by the pump (11) and then sent to the T-type bypassing tube (14). The T-type bypassing device (14) further bypasses the second mixture into two portions, the first portion and the second portion. Since all the reactions in the present invention occur in liquid phases, in order to get a higher conversion rate, the first portion is sent to one from the middle to the lower portion of the reactive distillation device (1) for a further conversion, whereas the second portion is recycled to the distillation device (8) for a further separation of methanol and methyl acetate.

The temperature of the different sections in the reactive distillation device (1) varies with the amount of the feeding streams and is controlled by the re-boiling device disposed on the bottom thereof. Similarly, the respective temperatures of the different sections existing in the distillation device (8) are also controlled in the same way.

For saving the investing production cost, in the transesterification process of methyl acetate of the present invention, the packed range of the solid catalysts in the reactive distillation device (1) is either from the top of the middle portion thereof or from the top to the lower portion thereof. In the present invention, the utilized catalyst is Amerlyst® 15 sold by Rohm and Hass™ which is commonly used in the industry.

According to the preferred embodiments of the present invention, the operating temperature in the reactive distillation device (1) is in a range from 55° C. to 170° C. Besides, the operating temperature in the distillation device (8) is in a range from 55° C. to 65° C. Furthermore, the operating pressure of the reactive distillation device (1) and the distillation device (8) is in a range from 1 to 2 atmosphere pressure, whereas the reflux devices (3) and (10) are operated under the constant atmosphere pressure.

In the present invention, the number of the theoretical trays of the stripping trays in the reactive distillation device (1) is in a range from 5 to 20, the number of the theoretical trays of the rectifying trays therein is in a range from 3 to 10, and the number of the theoretical trays therein is in a ranged from 15 to 55. In addition, the number of the theoretical trays in the distillation device (8) is in a range from 10 to 25.

Embodiments

| Items | Embodiment I | Embodiment II |
|---|---|---|
| Mol. Composition of methyl acetate solution | 60% methyl acetate + 40% methanol | 60% methyl acetate + 40% methanol |
| Mol. Composition of n-butanol solution | 100% n-butanol | 100% n-butanol |
| The reactive distillation device (1) | | |
| No. of the reactive trays | 35 | 48 |
| No. of the rectifying trays | 5 | 5 |
| No. of the stripping trays | 8 | 7 |
| No. of trays that n-butanol feeds | 43th | 55th |
| No. of trays that methyl acetate feeds | X | 12th |
| No. of trays that a zeotrope feeds | 12th | 12th |
| The distillation device (8) | | |
| No. of total trays | 14 | 19 |
| No. of trays that methyl acetate feeds | 12th | X |
| No. of trays that reflux feeds | 5th | 8th |
| The amount of reflux | 112.45 (kmol/hr) | 109.64 (kmol/hr) |
| The purity of butyl acetate | 99 mol % | 99 mol % |
| The purity of methanol | 99 mol % | 99 mol % |

In the Embodiment I, the methyl acetate solution is fed to the distillation device (8); in the embodiment II, the methyl acetate solution is fed to the reactive distillation device (1).

In conclusion, although the reactive distillation system depends upon the plurality of reactive trays, the plurality of stripping trays and the plurality of rectifying trays to serve as the major reactive sections, they could be alternatively disposed independently by coupling to the reactive distillation device. As described above, the working performance disclosed in the present invention will not be specifically limited to the disclosed embodiments therein, and all the transesterification process of methyl acetate by means of the mentioned reactive distillation system, the reflux system and the distillation system and their equivalents will not go beyond the protecting scope of the present invention.

Therefore, the transesterification process of methyl acetate in the present invention achieves a more efficient transesterification without investing considerable production cost, and is performed by only combination of the reactive distillation device and the distillation device. The present reactive distillation device is disposed with three sections, the stripping section, the reactive section and the rectifying section. The reactive section is further disposed with a plurality of reactive trays which packed with solid catalysts. The reactive section is disposed in a portion being positioned from the upper portion, or the middle portion to the lower portion within the reactive distillation device. The rectifying section is disposed upon the reactive section and the stripping section is disposed therebeneath. The methyl acetate solution is fed to a portion of the reactive distillation device being positioned from the middle portion to the lower portion thereof, or alternatively, fed to a portion of the distillation device being positioned from the upper portion to the middle portion thereof. The alcohol reactant is fed to a portion of the reactive distillation device being positioned from the upper portion to the middle portion thereof. By reacting methyl acetate of the excess amount with the alcohol reactants, the alcohol reactants are almost consumed completely and immediately, whereby the ester product with high purity could be obtained from the bottom of the reactive distillation device. Furthermore, the mixtures formed by methyl acetate and methanol respectively existing on the top of the reactive distillation and the distillation device could be liquefied for the subsequent separation, and the methanol with high purity could be obtained from the bottom of the distillation device.

As compared with the transesterification process of methyl acetate proposed by Luyben et al., the transesterification process of methyl acetate in the present invention not only reduces the amount of the required steam and the amount of the catalysts required to be packed, but also enhances the economic value thereof.

Therefore, the present invention proposes an industrially applicable transesterification process of methyl acetate in consideration of the thermodynamic properties of the transesterification system. According to the present invention, an ester with 99% high purity and a methanol with 99% high purity are obtained together with low economic costs.

By virtue of the foregoing, the alcohol reactant could be ethanol, isopropanol, propanol, isobutanol, butanol, isoamyl alcohol, amyl alcohol, hexyl alcohol and so on, in the transesterification process of methyl acetate of the present invention to satisfy the necessities of the various desired ester products. By reacting the mentioned alcohols with methyl acetate, the respective ethyl acetate, isopropyl acetate, propyl acetate, isobutyl acetate, butyl acetate, isoamyl acetate, amyl acetate, hexyl acetate and so on, could be obtained. The following will interpret the present transesterification process of methyl acetate will be applicable to each of the mentioned alcohols to transesterify methyl acetate into another ester corresponding to the selected alcohol.

Ethanol

By reacting methyl acetate with ethanol, the ester product, ethyl acetate is generated correspondingly. In consideration of the physical properties of the transesterification system of methyl acetate into ethyl acetate in its entirety, the priority of the boiling points of each constituent existing therein is shown in Table (2).

TABLE (2)

| Constituents | Boiling Point (° C.) |
| --- | --- |
| Methanol/Methyl acetate | 53.57 |
| Ethanol/Methyl acetate | 57.05 |
| Methyl acetate | 57.05 |
| Methanol/Ethyl acetate | 62.05 |
| Methanol | 64.53 |
| Ethanol/Ethyl acetate | 71.81 |
| Ethyl acetate | 77.20 |
| Ethanol | 78.31 |

According to Table (2), the possible azeotropes include four binary-components, methyl acetate/methanol, methyl acetate/ethanol, ethyl acetate/methanol and ethyl acetate/ethanol. The boiling point of the azeotrope formed by methyl acetate and methanol is the lowest, whereas the boiling point of ethanol is the highest and that of ethyl acetate is the second highest. However, ethanol is controlled as the limiting reagent in the transesterification process so it could be consumed completely and immediately after feeding without generation of the respective azeotropes, methyl acetate/ethanol and ethyl acetate/ethanol. Therefore, according to the transesterification process of methyl acetate in the present invention, the ethyl acetate of the second highest boiling point will be formed on the bottom of the reactive distillation device and obtained in high purity, and the methanol with high purity could be obtained from the bottom of the distillation system.

Isoproponal

By reacting methyl acetate with isopropanol, the ester product, isopropyl acetate is generated correspondingly. In consideration of the physical properties of the transesterification system of methyl acetate into isopropyl acetate in its entirety, the priority of the boiling points of each constituent existing therein is shown in Table (3).

TABLE (3)

| Constituents | Boiling Point (° C.) |
| --- | --- |
| Methanol/Methyl acetate | 53.57 |
| Methyl acetate | 57.05 |
| Methanol/Isopropyl acetate | 62.24 |
| Methanol | 64.53 |
| Isopropanol/Isopropyl acetate | 80.73 |
| Isopropanol | 82.35 |
| Isopropyl acetate | 88.52 |

According to Table (3), the possible azeotropes include three binary-components, methyl acetate/methanol, isopropyl acetate/methanol and isopropyl acetate/isopropanol, wherein methyl acetate is the lightest component and easily tends to form the azeotrope with methanol. The azeotrope of methyl acetate and methanol has the lowest boiling point so it is easily separated from isopropyl acetate. Furthermore, isopropanol is controlled as the limiting reagent so it could be consumed completely and immediately after feeding without generation of the azeotrope of isopropanol and isopropyl acetate. Regarding the azeotrope of methanol and isopropyl acetate, their co-boiling point could be easily broken through by the continuous heating process as well as the recirculation between the reactive distillation system and the distillation system. Therefore, according to the transesterification process of methyl acetate in the present invention, the isopropyl acetate of the highest boiling point will be formed on the bottom of the reactive distillation device and obtained in high purity, and the methanol with high purity could be obtained from the bottom of the distillation system.

Propanol

By reacting methyl acetate with propanol, the ester product, propyl acetate is generated correspondingly. In consideration of the physical properties of the transesterification system of methyl acetate into propyl acetate in its entirety, the priority of the boiling points of each constituent existing therein is shown in Table (4).

TABLE (4)

| Constituents | Boiling Point (° C.) |
| --- | --- |
| Methanol/Methyl acetate | 53.57 |
| Methyl acetate | 57.05 |
| Methanol/Propyl acetate | 62.24 |
| Methanol | 64.53 |
| Propanol/Propyl acetate | 94.74 |
| Propanol | 97.19 |
| Propyl acetate | 101.44 |

According to Table (4), the possible azeotropes include two binary-components, methyl acetate/methanol and propyl acetate/propanol, wherein methyl acetate is the lightest component and easily tends to form the azeotrope with methanol. The azeotrope of methyl acetate and methanol has the lowest boiling point so it is easily separated from propyl acetate. Furthermore, propanol is controlled as the limiting reagent so it could be consumed completely and immediately after feeding without generation of the azeotrope of propanol and propyl acetate. Regarding the azeotrope of methanol and propyl acetate, their co-boiling point could be easily broken through by the continuous heating process as well as the recirculation between the reactive distillation system and the distillation system. Therefore, according to the transesterification process of methyl acetate in the present invention, the propyl acetate of the highest boiling point will be formed on the bottom of the reactive distillation device and obtained in high purity, and the methanol with high purity could be obtained from the bottom of the distillation system.

Isobutanol

By reacting methyl acetate with isobutanol, the ester product, isobutyl acetate is generated correspondingly. In consideration of the physical properties of the transesterification system of methyl acetate into isobutyl acetate in its entirety, the priority of the boiling points of each constituent existing therein is shown in Table (5).

TABLE (5)

| Constituents | Boiling Point (° C.) |
| --- | --- |
| Methanol/Methyl acetate | 53.57 |
| Methyl acetate | 57.05 |
| Isobutanol/Isobutyl acetate | 98.36 |
| Isobutanol | 99.62 |
| Isobutyl acetate | 116.40 |

According to Table (5), the possible azeotropes include two binary-components, methyl acetate/methanol and isobutyl acetate/isobutanol, wherein methyl acetate is the lightest component and easily tends to form the azeotrope with the methanol. The azeotrope of methyl acetate and methanol has the lowest boiling point so it is easily separated from isobutyl acetate. Furthermore, isobutanol is controlled as the limiting reagent so it could be consumed completely and immediately after feeding without generation of the azeotrope of isobutanol and isobutyl acetate. Therefore, according to the transesterification process of methyl acetate in the present invention, the isobutyl acetate of the highest boiling point will be formed on the bottom of the reactive distillation device and obtained in high purity, and the methanol with high purity could be obtained from the bottom of the distillation system.

Isoamyl Alcohol

By reacting methyl acetate with isoamyl alcohol, the ester product, isoamyl acetate is generated correspondingly. In consideration of the physical properties of the transesterification system of methyl acetate into isoamyl acetate in its entirety, the priority of the boiling points of each constituent existing therein is shown in Table (6).

TABLE (6)

| Constituents | Boiling Point (° C.) |
| --- | --- |
| Methanol/Methyl acetate | 53.57 |
| Methyl acetate | 57.05 |
| Methanol | 64.53 |
| Isoamyl alcohol/Isoamyl acetate | 118.90 |
| Isoamyl alcohol | 119.01 |
| Isoamyl acetate | 141.66 |

According to Table (6), the possible azeotropes include two binary-components, methyl acetate/methanol and isoamyl acetate/isoamyl alcohol, wherein methyl acetate is the lightest component and easily tends to form the azeotrope with the methanol. The azeotrope of methyl acetate and methanol has the lowest boiling point so it is easily separated from isoamyl acetate. Furthermore, isoamyl alcohol is controlled as the limiting reagent so it could be consumed completely and immediately after feeding without generation of the azeotrope of isoamyl alcohol and isoamyl acetate. Therefore, according to the transesterification process of methyl acetate in the present invention, the isoamyl acetate of the highest boiling point will be formed on the bottom of the reactive distillation device and obtained in high purity, and the methanol with high purity could be obtained from the bottom of the distillation system.

Amyl Alcohol

By reacting methyl acetate with amyl alcohol, the ester product, amyl acetate is generated correspondingly. In consideration of the physical properties of the transesterification system of methyl acetate into amyl acetate in its entirety, the priority of the boiling points of each constituent existing therein is shown in Table (7).

TABLE (7)

| Constituents | Boiling Point (° C.) |
| --- | --- |
| Methanol/Methyl acetate | 53.57 |
| Methyl acetate | 57.05 |
| Methanol | 64.53 |
| Amyl alcohol | 137.68 |
| Amyl acetate | 147.71 |

According to Table (7), the possible azeotrope only includes one binary-component, methyl acetate/methanol, wherein methyl acetate is the lightest component and tends to form the azeotrope with the methanol. The azeotrope of methyl acetate and methanol has the lowest boiling point so it is easily separated from amyl acetate. Furthermore isoamyl alcohol is controlled as the limiting reagent so it could be consumed completely and immediately after feeding. Therefore, according to the transesterification process of methyl acetate in the present invention, the amyl acetate of the highest boiling point will be formed on the bottom of the reactive distillation device and obtained in high purity, and the methanol with high purity could be obtained from the bottom of the distillation system.

Hexyl Alcohol

By reacting methyl acetate with hexyl alcohol, the ester product, hexyl acetate is generated correspondingly. In consideration of the physical properties of the transesterification system of methyl acetate into hexyl acetate in its entirety, the priority of the boiling points of each constituent existing therein is shown in Table (8).

TABLE (8)

| Constituents | Boiling Point (° C.) |
| --- | --- |
| Methanol/Methyl acetate | 53.57 |
| Methyl acetate | 57.05 |
| Methanol | 64.53 |
| Hexyl alcohol/Hexyl acetate | 156.60 |
| Hexyl alcohol | 157.63 |
| Hexyl acetate | 171.20 |

According to Table (8), the possible azeotropes include two binary-components, methyl acetate/methanol and hexyl acetate/hexyl alcohol, wherein methyl acetate is the lightest component and easily tends to form the azeotrope with the methanol. The azeotrope of methyl acetate and methanol has the lowest boiling point so it is easily separated from hexyl acetate. Furthermore, hexyl alcohol is controlled as the limiting reagent so it could be consumed completely and immediately after feeding without generation of the azeotrope of hexyl alcohol and hexyl acetate. Therefore, according to the transesterification process of methyl acetate in the present invention, the hexyl acetate of the highest boiling point will be formed on the bottom of the reactive distillation device and obtained in high purity, and the methanol with high purity could be obtained from the bottom of the distillation system.

From the mentioned description, the present transesterification process of the methyl acetate is capable of generating the desired ester product by means of selecting the corresponding alcohol as the reactants. There exists the consistence in each of the mentioned transesterification system that the boiling point of the azeotrope formed by methyl acetate and methanol is the lowest as well as the boiling point of ester product is the highest. Such consistence is beneficial to the present transesterification process of the methyl acetate. Moreover, the present transesterification process of methyl acetate takes the alcohol reactants as the limiting reagent, which the alcohol reactant reacts with the methyl acetate of the excess amount, so that the alcohol reactant is almost completely consumed. Accordingly, the azeotropes formed by the alcohol reactant almost fail to be generated, and the ester product of the highest boiling points will be obtained from the bottom of the reactive distillation device.

In view of the above, the transesterification process of methyl acetate in the present invention is capable of being applicable to various kinds of alcohols to transesterify methyl acetate into the corresponding esters. In addition, the transesterification process provided in the present invention could highly reduce the investing production cost of the transesterification of the by-product, methyl acetate, in the conventional polyvinyl alcohol plants.

While the invention has been described in terms of what is presently considered to be the most practical and preferred embodiments, it is to be understood that the invention needs not be limited to the disclosed embodiments. On the contrary, it is intended to cover various modifications and similar arrangements included within the spirit and scope of the appended claims which are to be accorded with the broadest interpretation so as to encompass all such modifications and similar structures.

What is claimed is:

1. A transesterification process of a methyl acetate, comprising:
   (a) performing a first reactive distillation of a methyl acetate solution and a first alcohol to generate a first ester and a first mixture;
   (b) performing a first distillation of a first part of the first mixture to generate a second mixture;
   (c) performing a second reactive distillation of a first part of the second mixture and a second alcohol to generate a second ester; and
   (d) performing a third reactive distillation of a second part of the first mixture and a third alcohol to generate a third ester,
   wherein the respective one of the first and second alcohols is a limiting reagent.

2. A process as claimed in claim 1, wherein the methyl acetate solution includes a 40 mol % methanol.

3. A process as claimed in claim 1, wherein the respective reactive distillation is operated in a temperature ranged from 55° C. to 170° C. and the step (b) is operated in a temperature ranged from 55° C. to 65° C.

4. A process as claimed in claim 1, wherein the respective reactive distillation and the distillation are operated in a pressure ranged from 1 to 2 atmosphere pressure.

5. A process as claimed in claim 1, wherein the first, second and third alcohols are ones selected from a group consisting of an ethanol, an isopropanol, a propanol, an isobutanol, a butanol, an isoamyl alcohol, an amyl alcohol, and a hexyl alcohol, and the first, second and third esters are the same ester.

6. A process as claimed in claim 1, wherein the step (b) further comprises generating a first methanol therefrom and a step of:
   performing a second distillation of a second part of the second mixture to generate a second methanol.

7. A transesterification process of a methyl acetate, comprising:
   (a) reacting a methyl acetate solution with a first alcohol in a reactive distillation device to generate a first mixture and a first ester;
   (b) performing a first distillation of a first part of the first mixture in a distillation device to generate a second mixture;
   (c) refluxing a second part of the first mixture to the reactive distillation device for a reactive distillation reaction with a third alcohol,
   (d) reacting a first part of the second mixture and a second alcohol in the reactive distillation device to generate a second ester,
   wherein the respective one of the first and the second alcohols is a limiting reagent.

8. A process as claimed in claim 7, wherein the first, second and third alcohols are ones selected from a group consisting of an ethanol, an isopropanol, a propanol, an isobutanol, a butanol, an isoamyl alcohol, an amyl alcohol, and a hexyl alcohol, and the first and the second esters are the same ester.

9. A process as claimed in claim 7, wherein the step (b) further comprises generating a first methanol and the step (d) further comprises a step of:
   performing a second distillation of a second part of the second mixture to generate a second methanol.

10. A process as claimed in claim 7, wherein the reactive distillation device comprises a plurality of reactive trays, a plurality of stripping trays and a plurality of rectifying trays, a number of the plurality of reactive trays is ranged from 15 to 55, a number of the plurality of stripping trays is ranged from 3 to 10, and a number of the plurality of rectifying trays is ranged from 5 to 20.

11. A process as claimed in claim 7, wherein the alcohols are fed from an upper portion of the reactive distillation device and the methyl acetate solution is fed from a portion being positioned from a middle portion to a lower portion of the reactive distillation device.

12. A transesterification process of a methyl acetate, comprising:
   (a) performing a first distillation of a methyl acetate solution to generate a first methanol and a first mixture;
   (b) performing a first reactive distillation of a first part of the first mixture and a first alcohol to generate a first ester and a second mixture;
   (c) performing a second distillation of a first part of the second mixture to generate a second methanol; and
   (d) performing a third distillation of a second part of the first mixture to generate a third methanol,
   wherein the first alcohol is a limiting reagent.

13. A process as claimed in claim 12, further comprising a step of:
   (e) performing a second reactive distillation of a second part of the second mixture and a second alcohol to generate a second ester.

14. A process as claimed in claim 13, wherein the first and second alcohols are ones selected from a group consisting of an ethanol, an isopropanol, a propanol, an isobutanol, a butanol, an isoamyl alcohol, an amyl alcohol, and a hexyl alcohol, and the first and the second esters are the same ester.

15. A process as claimed in claim 13, wherein the first and the second reactive distillations are performed in a reactive distillation device.

16. A process as claimed in claim 15, wherein the alcohols are fed from an upper portion of the reactive distillation device and the methyl acetate solution is fed from an upper portion of the distillation device.

17. A process as claimed in claim 16, wherein the reactive distillation device comprises a plurality of reactive trays, a plurality of stripping trays and a plurality of rectifying trays, and a number of the plurality of reactive trays is ranged from 15 to 55, a number of the plurality of stripping trays is ranged from 3 to 10, and a number of the plurality of rectifying trays is ranged from 5 to 20.

* * * * *